US00PP34399P2

(12) United States Plant Patent
Breen et al.

(10) Patent No.: US PP34,399 P2
(45) Date of Patent: Jul. 5, 2022

(54) APPLE TREE NAMED 'SF1'

(50) Latin Name: *Malus domestica*
Varietal Denomination: 'SF1'

(71) Applicant: The New Zealand Institute for Plant and Food Research Limited, Auckland (NZ)

(72) Inventors: Kenneth Charles Breen, Hastings (NZ); Nicholas Anderson, Othello, WA (US)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 17/300,877

(22) Filed: Dec. 3, 2021

Related U.S. Application Data

(60) Provisional application No. 63/121,859, filed on Dec. 4, 2020.

(51) Int. Cl.
*A01H 6/74* (2018.01)
*A01H 5/08* (2018.01)

(52) U.S. Cl.
USPC ..... Plt./161

(58) Field of Classification Search
USPC ..... Plt./161
See application file for complete search history.

*Primary Examiner* — Annette H Para
(74) *Attorney, Agent, or Firm* — Leydig, Voit & Mayer, Ltd.

(57) ABSTRACT

A new and distinct variety of apple tree is described. The variety results from a limb sport found in Washington, United States. The fruit of the apple tree of this new variety have an attractive appearance, characterised by a high proportion of red over color and an over color pattern that is a solid flush with weakly defined stripes.

6 Drawing Sheets

Genus and species plant claimed: *Malus domestica.*
Variety denomination: 'SF1'.

BACKGROUND OF THE INVENTION

The new variety of 'SF1', *Malus domestica*, resulted from a spontaneous limb sport mutation of 'Scifresh' (U.S. Plant Pat. No. 13,888). The 'Scifresh' tree containing the limb sport of the new variety was discovered in 2011, growing in a cultivated area in Washington, USA. It was selected for further observation because of its fruit skin color. 'SF1' was first asexually propagated in 2011 in Washington, USA by budding onto rootstocks 'Nic19' and these resulting trees were planted in an orchard in Washington in 2013. Further propagation of the selection occurred, and more trees were planted in 2015, 2018 and 2019 in Washington. The resulting plants were found to be true to type demonstrating that the characteristics of the new variety 'SF1' are stable and transmitted without change through succeeding generations.

SUMMARY OF THE INVENTION

'SF1' can be characterised by its medium sized fruit (197 g) with fruit red skin (near red, 53A) over color pattern that is a solid flush with weakly defined stripes.

'SF1' is distinguished from its parent, 'Scifresh' by the following characteristics:

'SF1' has on average a higher percentage of fruit skin over color (96%) compared to 'Scifresh' (73%). In addition, SF1's red skin over color (near red, 53A) has a darker intensity compared to 'Scifresh's over color', which is near 42D.

BRIEF DESCRIPTION OF THE DRAWINGS

The accompanying photographs show typical specimens of the tree and fruit of the new variety as depicted in colors as nearly true as is reasonably possible to make the same in a color illustration of this character.

DETAILED DESCRIPTION

Figure 1:
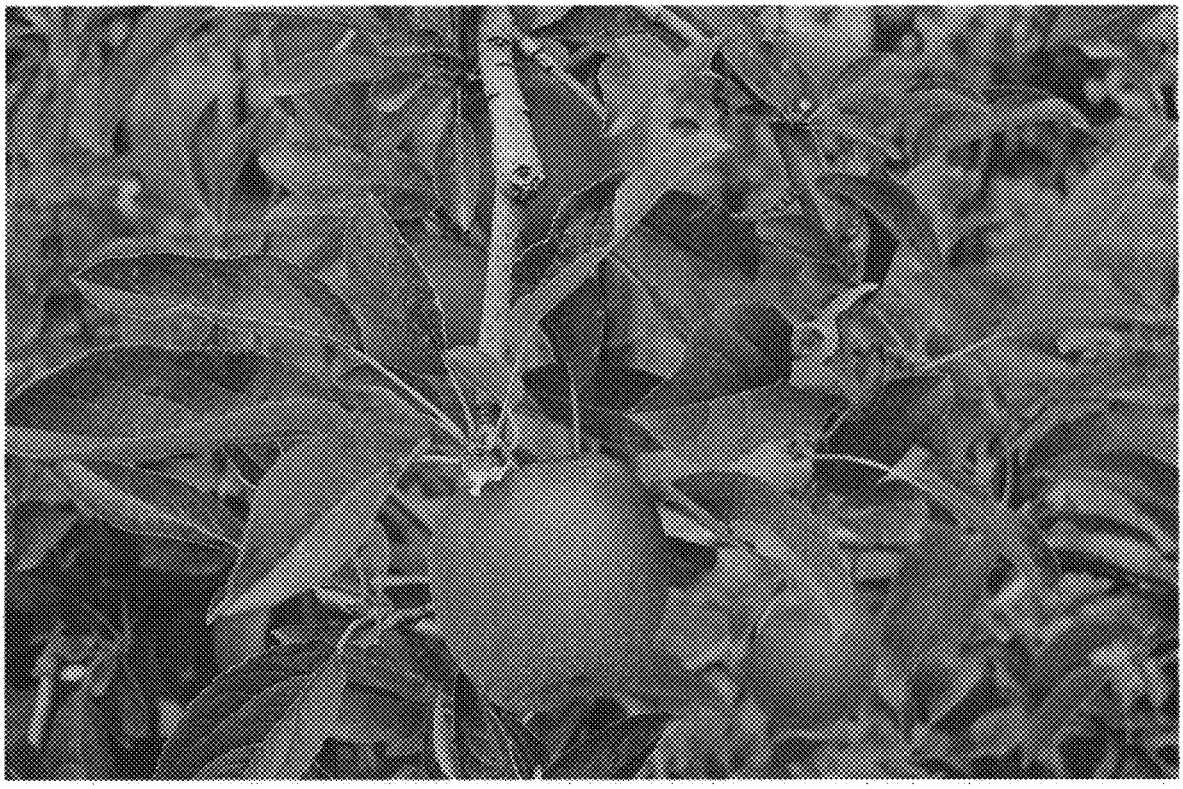
FIG. 1 shows 'SF1' fruit on tree
Figure 2:
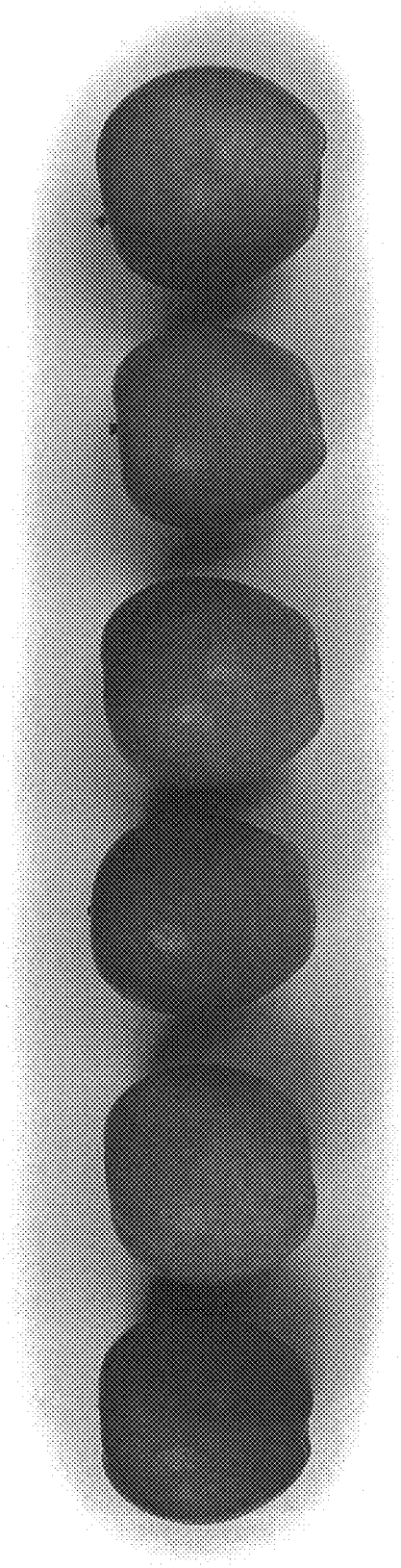
FIG. 2 shows 'SF1' fruit lateral view
Figure 3:
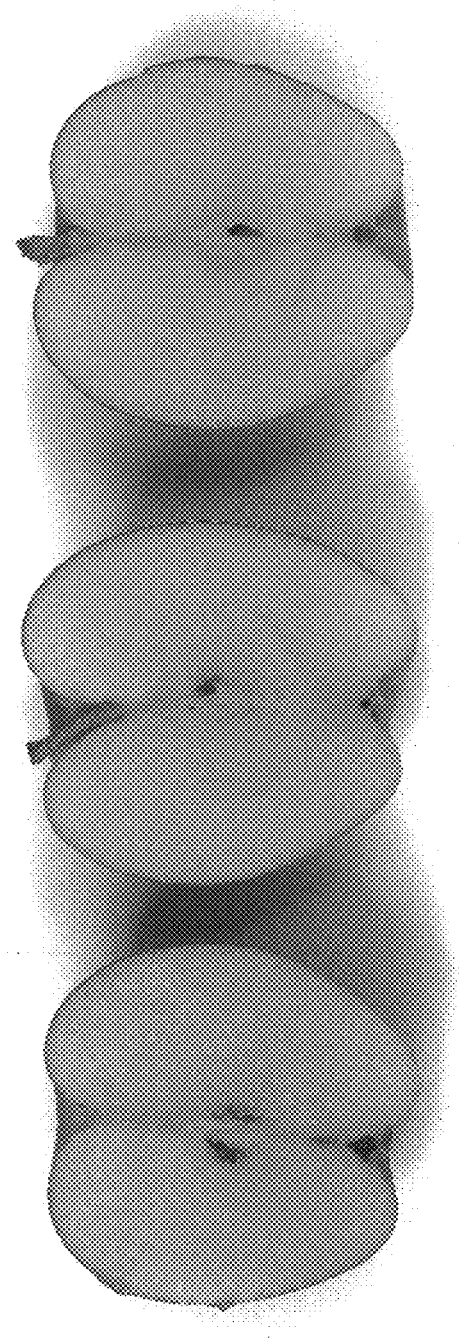
FIG. 3 shows 'SF1' longitudinal section of cut fruit
Figure 4:
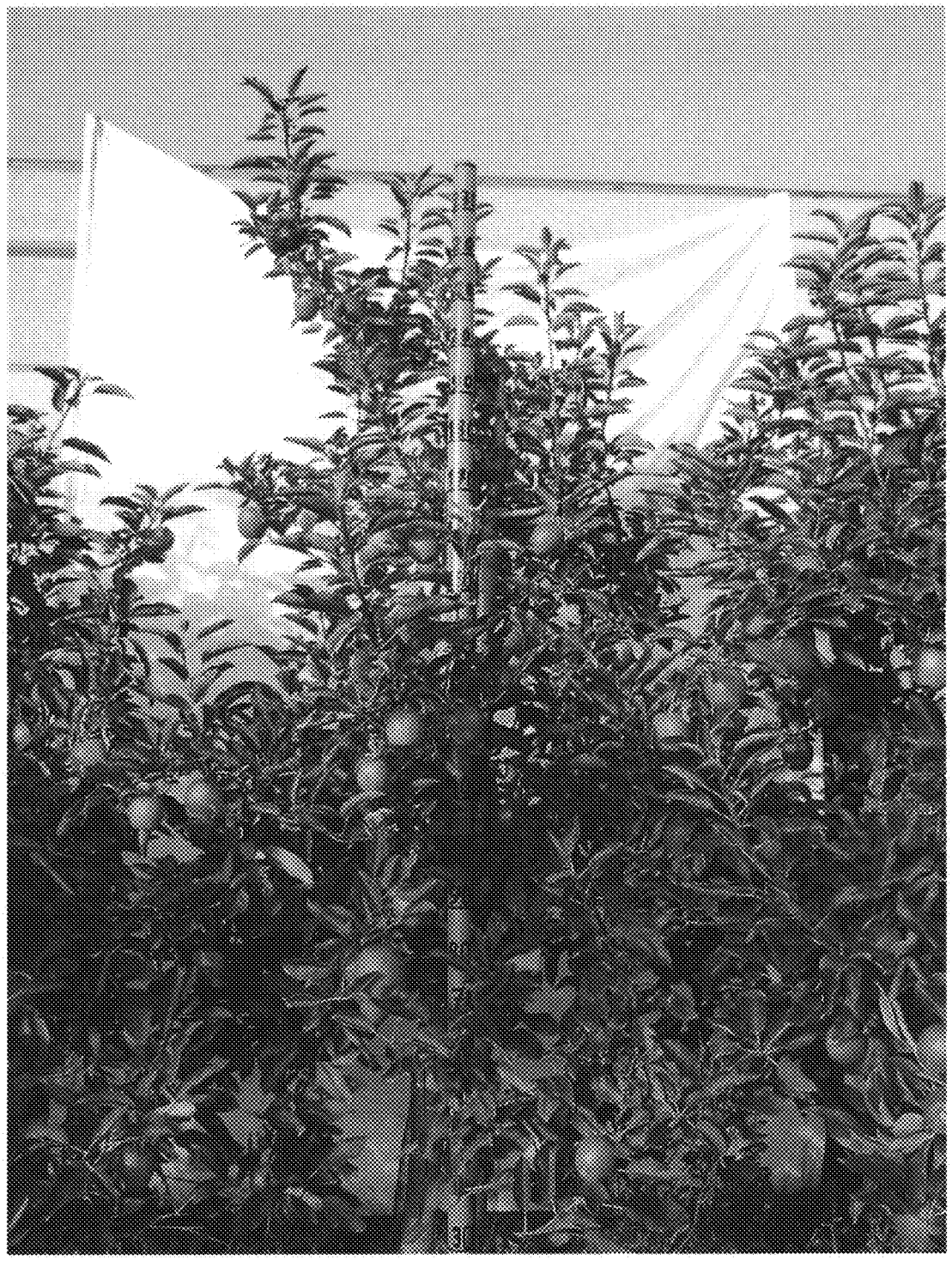
FIG. 4 shows a 'SF1' 4-year-old tree
Figure 5:
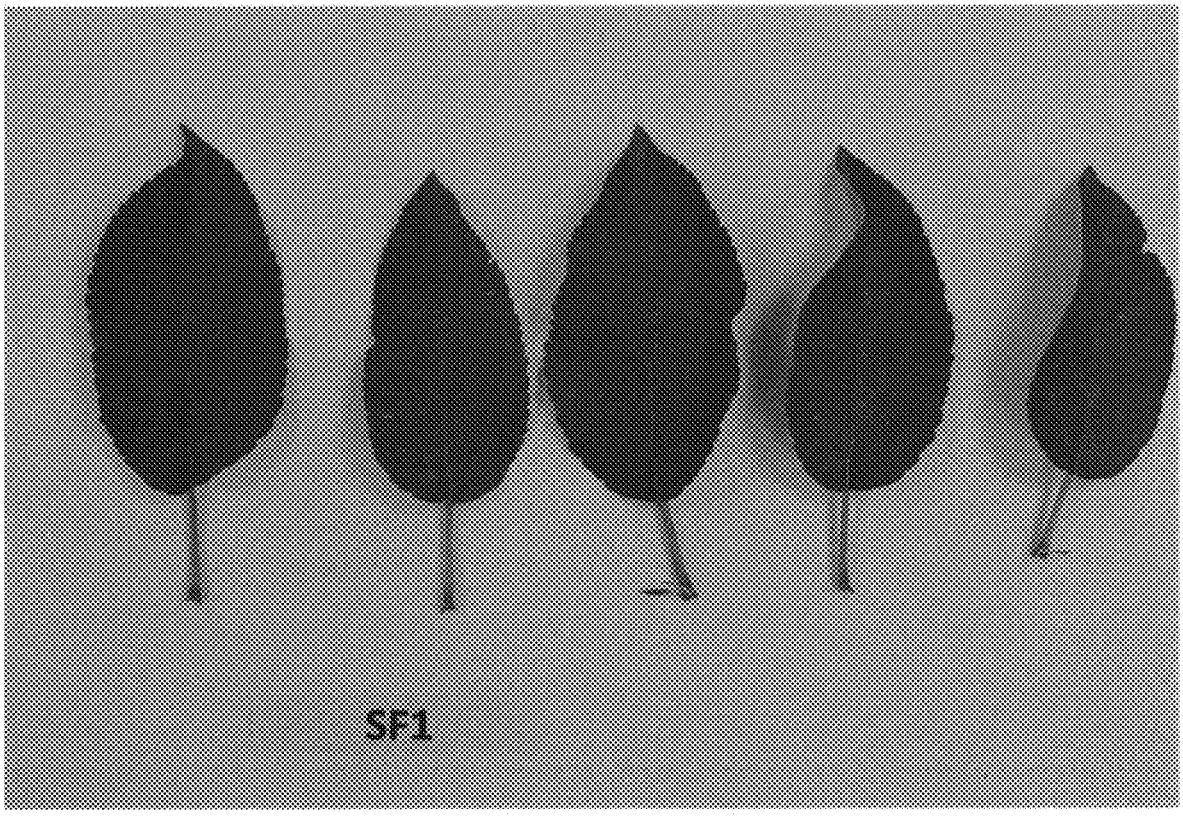
FIG. 5 shows 'SF1' top side of leaves
Figure 6:
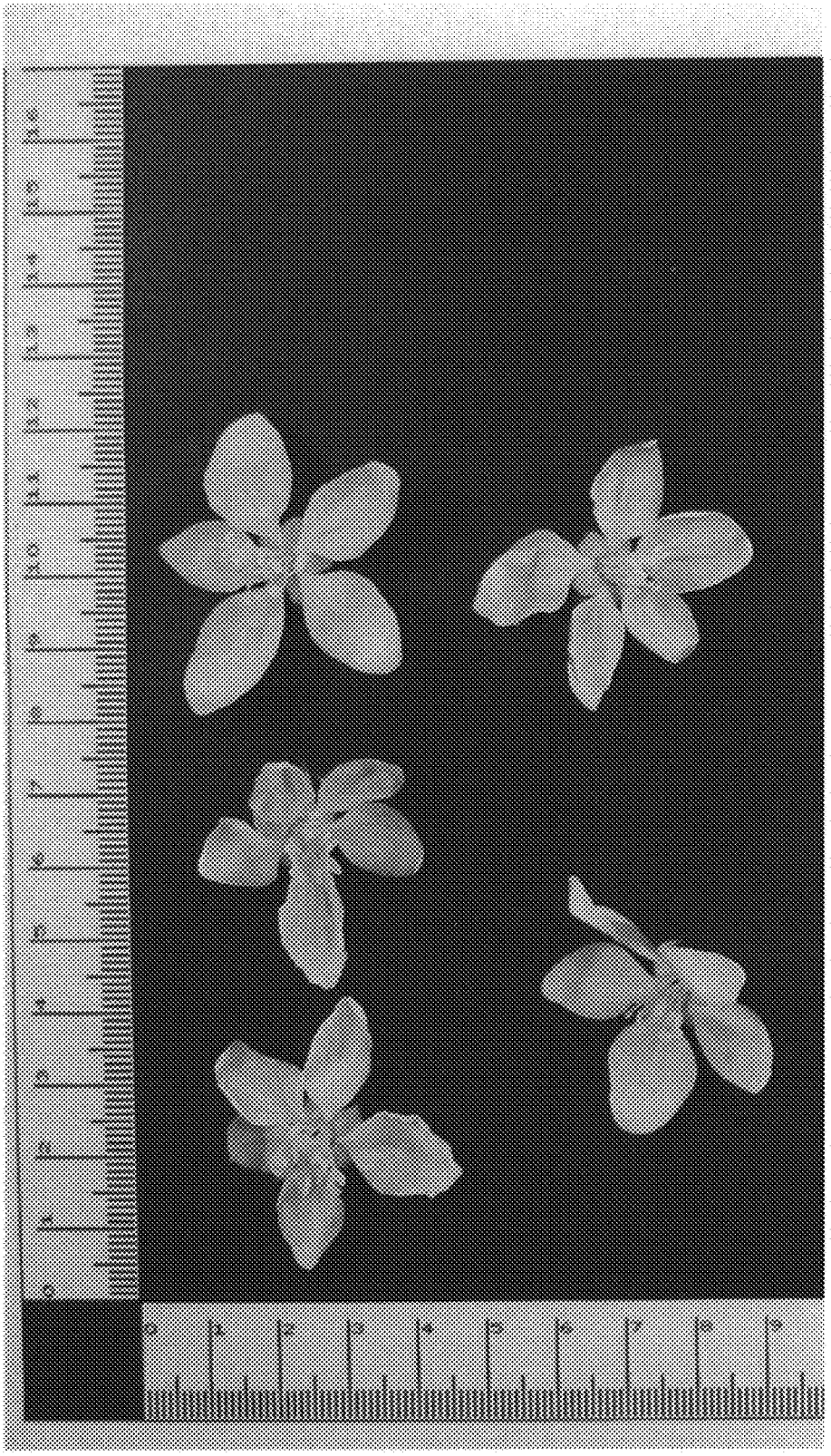
FIG. 6 shows 'SF1' flowers

The following is a detailed description of SF1 with color terminology in accordance with The Royal Horticultural Society Color Charts (R.H.S.C.C) fifth edition.

The specimens described were grown at Angers, France. The observations were made over two seasons from 2019-2020 on 3-4 year old trees on 'M9' rootstock. It should be understood that that the characteristics described will vary somewhat depending on cultural practices and climate conditions and will also vary depending upon location and season. Quantified measurements are generally expressed an average of measurements taken from individual trees of SF1 unless otherwise noted. However, the measurements of any individual plant or any group of plants of SF1 may vary from the stated average.

Information on the breeding scheme and propagation of the variety:

Characteristics of the variety: Tree type: ramified habit; approximately 2.7 m tall and 1.7 m wide; spreading habit; bearing on spurs and long shoots; medium vigour on 'M9', managed under standard orchard practice.

Trunk: Measurements were taken 20 cm from the graft union. Trunk circumference was approximately 12.4 cm; color near dark grey 197C; bark texture slightly rough.

One year old shoot: Approximately 30 cm long; medium thickness, averaging 5-6 mm with straight growth; color on the sunny side near medium brown, 200A; average internode length 2 cm; number of lenticels was medium, averaging 7/cm$^2$, elliptical to irregular round in shape and near greyed white in color, 156C; on the distal half of the shoot a medium amount of pubescence was present.

Vegetative bud: Approximately 6.3 mm long; acute shape and near brown 200A color; in relation to the shoot is adpressed to slightly held out.

Leaf blade: Average length 8.5 cm; average width 4.3 cm at the widest point; weak pubescence on the lower side; basal shape obtuse; apex shape acute; margin of the leaves crenate, the attitude in relation to the shoot outwards; color on upper side near dark green 147A; color on the underside near green 148C; color of the venation near light green 145C.

Petiole: Average length 26 mm; average width 3 mm; color on the upper side near green 139D and color on the underside near yellow green 145C.

Stipule: Average stipule length 4.4 mm; average width 1.1 mm; color on the upper side was near yellow green 147B; under side color near green 138C.

Flowers: Predominate color at balloon stage near dark pink, near 52A; diameter of the open flower approximately 37 mm; an average of 5 flowers were present per cluster; location of flower bud mainly on spurs; fragrance present.

Petals: 5 petals per flower with an ovate shape; arrangement of petals intermediate; average length 18.1 mm; average width 10.9 mm; rounded base; lower surface color near red purple, 61C and 63B; near red purple veins, 71B and 67A; average length of the petal claw 1.8 mm.

Stamen: Average of 17 per flower; filaments average length 5.3 mm and near white in color, 155D; anthers average length 2.8 mm, color near yellow, 4D; pollen color near yellow, 7D.

Pistil: Average length 9.5 mm; color near light green, 145C; position of stigmas in relation to anthers: above.

Pedicel: Average length 16.6 mm; average diameter 1.6 mm; color near yellow green, 152B.

Sepals: Five sepals per flower; average length 7.3 mm and average width 3.9 mm; color near yellow green, 145A; Attitude of sepals in relation to corolla recurved.

Fruit size: Medium; average width 74.5 mm; average height 74.2 mm; average weight 197 g.

Fruit shape: Most fruit tending to be conic in shape; position of maximum diameter middle; crowning at calyx absent to very weak; eye basin average depth 10.2 mm; average width 26.6 mm; ribbing absent; average length of sepals 5 mm.

Fruit skin: Bloom absent to very weak; greasiness absent to very weak; background color near yellow, 4A; size of lenticels small.

Fruit over color: Very large amount of over color, approximately 96%; near red, 53A, with medium to dark intensity; pattern of over color solid flush with weakly defined stripes; width of the stripes narrow; russet absent or very small amount around stalk attachment, on cheeks and around eye basin.

TABLE 1

Table showing the distinguishing characters between 'SF1' and 'Scifresh', observations made on trees Angers, France over 2 seasons, 2019 and 2020 on trees aged 3-4 years on 'M9' rootstock.

| Distinguishing Characteristics | 'SF1' | 'Scifresh' |
|---|---|---|
| Over color hue with bloom removed | Near 53A | Near 42D |
| Relative area of over color | Very large - on average approximately 96% | Medium on average approximately 73% |
| Ground colour of skin | Yellow, Near 4A | Yellow green, Near 154D |

Fruit stalk: Average length 16.8 mm; average width 4 mm; average depth of stalk cavity 12.3 mm; average width 30.6 mm; curvature of stalk absent or very weak.

Fruit flesh: Firm, average fruit firmness 9.6 kgf; near yellow white in color, 158A; aperture of locules in transverse section closed or slightly open.

Fruit flavor: Medium sweetness; medium acidity; aroma rich; average soluble solids 13%.

Fruit seeds: Five locules; ovate shaped; average length 9 mm; average width 5 mm; color near greyed orange, 175A.

Harvest: Late September.

Use: Dessert.

Pest and disease tolerance/susceptibility: 'SF1' has not been observed to be any more or less tolerant or susceptible to any pest or diseases than 'Scifresh'.

The invention claimed is:

1. A new and distinct variety of apple tree substantially as illustrated and described herein.

* * * * *